United States Patent [19]

Troller

[11] 4,304,862
[45] Dec. 8, 1981

[54] METHOD FOR INCREASING THE DIACETYL PRODUCTION OF A DIACETYL-PRODUCING BACTERIA

[75] Inventor: John A. Troller, Cincinnati, Ohio

[73] Assignee: The Procter & Gamble Company, Cincinnati, Ohio

[21] Appl. No.: 151,004

[22] Filed: May 19, 1980

[51] Int. Cl.$^3$ .............................................. C12P 7/26
[52] U.S. Cl. .................................. 435/148; 435/244; 435/253; 435/885; 426/34
[58] Field of Search ............... 435/148, 244, 253, 885; 426/34, 43

[56] References Cited

U.S. PATENT DOCUMENTS

| | | | |
|---|---|---|---|
| Re. 28,488 | 7/1975 | Farr | 435/253 |
| 3,592,740 | 7/1971 | Christensen | 435/253 |
| 4,191,782 | 3/1980 | Vedamuthu | 435/885 X |
| 4,226,940 | 10/1980 | Storrs | 435/885 X |

FOREIGN PATENT DOCUMENTS

| | | |
|---|---|---|
| 933877 | 9/1978 | Canada . |
| 2813714 | 10/1979 | Fed. Rep. of Germany ........ 426/34 |
| 47-04996 | 2/1972 | Japan ..................................... 426/34 |
| 53-3029958 | 3/1978 | Japan . |

OTHER PUBLICATIONS

Troller, *Water Activity and Food,* 42–44, Academic Press, New York, (1978).
Vasil'ev et al., Chemical Abstracts 85:19253m, 520 (1976).
Silant'eva et al., Chemical Abstracts, 83:130171f, 386 (1975).
Sasaki et al., Chemical Abstracts 49:12740i (1953).
Winton, *The Structure and Composition of Foods,* vol. III, John Wiley & Sons, Inc. New York, 95, 96 (1937).

*Primary Examiner*—Esther M. Kepplinger
*Attorney, Agent, or Firm*—Eric W. Guttag; Rose Ann Dabek; Richard C. Witte

[57] ABSTRACT

A method for increasing the diacetyl production of a diacetyl-producing bacteria such as *Streptococcus diacetylactis.* Glycerol or sucrose as humectants are added to an aqueous nutrient medium such as milk having a 2% butterfat content which contains a diacetyl precursor such as sodium citrate. The bacteria are then inoculated into the humectant-containing nutrient medium. The humectant lowers the $a_w$ value of the nutrient medium so as to increase the diacetyl production of the bacteria when incubated at a temperature of from 28° to 37° C.

18 Claims, No Drawings

METHOD FOR INCREASING THE DIACETYL PRODUCTION OF A DIACETYL-PRODUCING BACTERIA

TECHNICAL FIELD

The present application relates to diacetyl production and in particular to a method for increasing the diacetyl production of bacteria such as *Streptococcus diacetylactis*.

BACKGROUND ART

There are a number of compounds which make up butter flavor and aroma. Probably the most important group of compounds are the lower carboxylic acids such as acetic, propionic, butyric and caproic acids. Other important components of butter flavor include the methyl ketones and lactones. See U.S. Pat. No. 2,819,169 to Boldingh, issued Jan. 7, 1958 which discloses that the lactones, especially the gamma variety, impart butter-like flavors to oleaginous compositions.

Another important component of butter aroma is the compound diacetyl (2,3-butanedione). This compound is a yellow liquid having an extremely potent butter aroma. Diacetyl can be formed via two different methods. The first method involves chemical synthesis. For example, diacetyl can be synthesized from methyl ethyl ketone by conversion to an isonitroso compound which is then decomposed by hydrolysis with hydrochloric acid to diacetyl. See the Merck Index (8th Ed. 1968), page 337.

A second method for producing diacetyl is by bacterial fermentation. For example, glucose can be fermented to methylacetylcarbinol which is then oxidized to form diacetyl. See the Merck Index (8th Ed. 1968), page 337. See also U.S. Pat. No. 2,586,072 to Marcoux, issued Feb. 19, 1952 which discloses production of diacetyl from a bacterial culture such as *S. diacetylactis* incubated at temperatures of from 70° to 80° F. until titratable acidity of 0.55% lactic acid is present. A method which would increase the diacetyl production of a bacterial culture would therefore be desirable.

It is therefore an object of the present invention to provide a bacterial diacetyl-producing composition.

It is yet a further object of the present invention to provide a method for increasing the diacetyl production of diacetyl-producing bacteria.

These and further objects of the present invention are hereinafter disclosed.

DISCLOSURE OF THE INVENTION

A. Summary of the Invention

The present invention relates to a novel composition wherein the diacetyl-producing capacity of diacetyl-producing bacteria is substantially increased per volume of nutrient medium. The diacetyl-producing composition includes an aqueous nutrient medium having a pH of from about 4.5 to 7.0 and containing a metabolizable amount of a diacetyl precursor. The composition further includes a bacterium selected from *S. diacetylactis*, *Streptococcus cremoris*, *Streptococcus lactis* or mixtures of these bacteria. Most importantly, the composition includes an humectant selected from glycerol, sucrose and mixtures thereof in an amount sufficient to lower the $a_w$ value of the nutrient medium to from about 0.95 to 0.99 and to increase the production of diacetyl by the bacteria per volume of nutrient medium. The diacetyl-producing composition is incubated at a temperature of from about 28° to 37° C. to produce the diacetyl.

A number of methods have been tried for increasing the production of diacetyl of a bacterial culture. For example, the diacetyl production rate of *S. citrovorus* and *S. paracitrovorus* bacterial cultures is increased when the cultures are maintained under pressure and air is stirred or bubbled through the cultures. See U.S. Pat. No. 2,196,239 to Werkman, issued Apr. 9, 1949. Another possible method for increasing diacetyl production is by elevating the solids content of the nutrient medium. See Chem. Abstracts 85:19253m (1976) which indicates that greater amounts of flavor compounds are formed in milk fermented by lactic acid bacteria when the solids content is elevated. See also Chem. Abstracts 83:130171f (1975) which indicates that increases in solids content of milk activates lactic acid bacteria and contributes to the development of the organoleptic properties of sour milk. The effect of various saccharide compounds on the diacetyl production rate of *S. lactis* and *S. cremoris* has also been investigated. See Chem. Abstracts 49:12740i (1955) which indicates that diacetyl production is increased in the order of lactose>galactose>glucose. By contrast, it has been specifically found according to the present invention that glycerol or sucrose are effective to increase diacetyl production of bacteria such as *S. diacetylactis* when added in specified amounts to lower the $a_w$ value of the nutrient medium.

It has also been determined that glycerol and sucrose do not act as nutrients for the diacetyl-producing bacteria. Instead, it has been found that these compounds act as humectants to lower the $a_w$ value of the nutrient medium. See J. A. Iroller and J. H. B. Christian, *Water Activity and Food* (1978) (hereinafter referred to as *Water Activity*), pp. 42–44 which discloses that glycerol and sucrose are often used to lower $a_w$ levels in foods. It has further been surprisingly and unexpectedly found that as the $a_w$ value of the nutrient medium is lowered, the diacetyl production by the specified bacteria is increased per volume of nutrient medium, even though the growth rate of the bacteria generally decreases. Because sodium chloride, a known humectant for lowering $a_w$ values of foods, does not increase diacetyl production of the specified bacteria, there is apparently some selectivity with regard to employment of glycerol or sucrose in diacetyl-producing compositions of the present invention.

B. Nutrient Medium

A variety of nutrient media can be employed in the diacetyl-producing compositions of the present invention. Generally, the nutrient medium must be aqueous. Also, the nutrient medium must contain naturally, or by addition, a metabolizable amount of a diacetyl precursor. As used herein, the term "diacetyl precursor" refers to a raw material which the diacetyl-producing bacteria metabolizes to form diacetyl, the metabolite. Preferred precursors include citric acid and bacteriologically acceptable salts of citric acid. A particularly preferred precursor because of its commercial availability is sodium citrate. As used herein, the term "metabolizable amount" refers to a sufficient amount of diacetyl precursor such that measurable amounts of diacetyl are formed by the bacteria. Typically, the amount of the precursor can range from about 0.1 to 1.0% by weight of the nutrient medium.

A preferred nutrient medium is milk containing up to about 2% butterfat, plus additional diacetyl precursor such as sodium citrate.

C. Diacetyl-Producing Bacteria

Diacetyl-producing bacteria which can be employed in the diacetyl-producing compositions of the present invention are *S. diacetylactis*, *S. cremoris*, *S. lactis* and mixtures of any of the foregoing bacteria. A description of the foregoing three bacteria can be found in *Bergey's Manual of Determinative Bacteriology* (8th ed. 1974), pp. 507-508. The diacetyl-producing capacity of *S. diacetylactis* is much more improved by the addition of glycerol or sucrose compared to the other two bacteria and is therefore preferred in diacetyl-producing compositions of the present invention for this reason.

D. Humectants and $A_w$ Values

It has been found that glycerol or sucrose are effective in increasing the diacetyl production of bacteria employed in compositions of the present invention. Further, these two compounds are employed in specified amounts in order to increase the diacetyl-producing capacity of the bacteria. The method for determining when sufficient amounts of the humectant have been added to the nutrient medium is by measuring $a_w$ values of the nutrient medium containing the humectant. As used herein, the term "$a_w$ value" refers to the amount of free or unbound water contained within the nutrient medium. See Water Activity, supra, pp. 1-11, for a further description and definition of $a_w$ values. In the case of a pure water solution, the $a_w$ value is 1.00. For nutrient media employed in compositions of the present invention, the $a_w$ value is close to about 0.998 when the humectants are not present. Because $a_w$ values are strongly affected by temperature differences, the $a_w$ values of nutrient media referred to in the present application, with or without humectants, are measured at 25° C. and prior to inoculation of the medium with the diacetyl-producing bacteria.

It has been found that glycerol or sucrose, when added in amounts sufficient to lower the $a_w$ value of the nutrient medium to from about 0.95 to 0.99, increase the diacetyl production of the bacteria. It is to be understood that the foregoing $a_w$ value range normally sets the outer limits within which sucrose or glycerol are effective to increase diacetyl production of the bacteria. The effective $a_w$ values for the nutrient medium can vary depending on which humectant is employed and which bacteria are inoculated into the nutrient medium. However, the effective $a_w$ values for each humectant with regard to each of the bacteria can be readily determined by comparing the diacetyl production of the composition containing humectant with that of a diacetyl-producing composition which does not contain humectant. It is only those humectant-containing diacetyl-producing compositions which have increased diacetyl-producing capacity per volume of nutrient medium which are claimed herein. Generally, an $a_w$ value of from about 0.95 to 0.97 when glycerol is the humectant is sufficient to increase the diacetyl production of the bacteria. In the case of sucrose, an $a_w$ value of from about 0.97 to 0.99 is sufficient to increase diacetyl production of all the bacteria except *S. diacetylactis* wherein the $a_w$ value usually needs to be about 0.99.

The ability of glycerol or sucrose when added in specified amounts to the nutrient medium to increase diacetyl production of the specified bacteria is particularly surprising in view of the effect that decreasing $a_w$ values have on bacterial growth. It has been found that, generally, as the $a_w$ value of the nutrient medium decreases, the growth rate of the bacteria likewise decreases. For sucrose, growth of the bacteria generally ceases at an $a_w$ value of 0.93 except in the case of *S. lactis* where growth stops at an $a_w$ value of 0.95. For glycerol, which is less growth inhibitory, bacterial growth stops at an $a_w$ value of 0.93, except in the case of *S. lactis* where growth stops at an $a_w$ value of 0.91. Even though lower $a_w$ values generally decrease the growth rate of the diacetyl-producing bacteria, surprisingly, the capacity of the bacteria to produce diacetyl generally increases until the $a_w$ value reaches the point of no growth.

E. pH, Temperature and Method for Forming diacetyl-Producing Compositions

The pH of the nutrient medium of the diacetyl-producing composition of the present invention can range from about 4.5 to 7.0. A pH below about 4.5 is generally too acidic for the diacetyl-producing bacteria to grow in. A pH of above about 7.0 causes the bacteria to stop growing. Generally, as the $a_w$ value of the nutrient medium decreases, the final pH of the medium increases because of the lower growth rate of the bacteria and hence lower rate of production of lactic acid.

The diacetyl-producing compositions of the present invention can generally be produced as follows. A given amount of humectant is added to the nutrient medium to provide the desired $a_w$ value. The nutrient medium is then inoculated with the diacetyl-producing bacteria by methods generally known to the art of bacteriology. The inoculated medium is then incubated at a temperature of from about 28° to 37° C. Incubation time can vary to upwards of 120 hours or longer. Generally, the longer the incubation time, the more diacetyl is formed.

Best Mode

The following description is intended to illustrate the present invention and is not limiting thereof.

A. $A_w$ Values of Nutrient Media Containing Various Levels of Humectant

The $a_w$ values of aqueous nutrient medium (homogenized milk having 2% butterfat plus 0.5% sodium citrate by weight) containing varying amounts of glycerol or sucrose are shown in the following table:

TABLE 1

| | | g./100 ml. of nutrient medium | |
|---|---|---|---|
| | $A_w$ Value | Sucrose | Glycerol |
| Control | (0.998)[a] | 0. | 0. |
| | 0.99 | 18.3 | 2.0 |
| | 0.97 | 38.8 | 12.0 |
| | 0.95 | 49.9 | 21.5 |
| | 0.93 | 68.8 | 31.0 |
| | 0.91 | 87.7 | 40.5 |

[a]Nutrient medium without humectant $A_w$ values were determined at 25° C. with a Sina hygrometer operated and calibrated as described in a publication to John A. Troller, "Statistical Analysis of $A_w$ Measurements Obtained with the Sina Scope", *Journal of Food Science*, Vol. 41, pp. 86-89 (1977), herein incorporated by reference.

B. Growth characteristics of Diacetyl-Producing Bacteria in Nutrient Media Having Different $A_w$ Values The diacetyl-producing bacteria were obtained from dairy cultures whose identity was confirmed according to the method described in Reddy et al, "Differential Agar Medium for Separating Streptococcus Lactis and Streptococcus Cremoris", *Applied Microbiology*, Vol. 18 (1969), pp. 775–759. The bacteria were stored on All Purpose Medium with Tween 80 (APT) agar slants at 5° C. and subcultured for 24 hours at 32° C. in APT broth. The bacteria were then inoculated by pipetting a subculture thereof into 300 ml. of a nutrient medium consisting of homogenized pasteurized milk containing 2% butterfat supplemented with 0.5% by wt. sodium citrate. The inoculated medium was incubated at 32° C. for 120 hours.

The growth characteristics of the diacetyl bacteria in the various nutrient media are shown in the following table:

TABLE 2

| Bacteria | $A_w$ Value | Humectant | Growth Rate Div./Hr. | Log Max. No./ml.[1] |
|---|---|---|---|---|
| S. diacetylactis | 0.998 | Control[3] | 0.57 | 7.46 |
|  | 0.99 | Glycerol | 0.67 | 7.47 |
|  | 0.97 | Glycerol | 0.68 | 7.41 |
|  | 0.95 | Glycerol | 0.27 | 7.34 |
|  | 0.93 | Glycerol | No Growth | 4.34[2] |
|  | 0.91 | Glycerol | No Growth | 4.34[2] |
| S. Lactis | 0.998 | Control[3] | 0.71 | 8.41 |
|  | 0.99 | Glycerol | 0.91 | 8.39 |
|  | 0.97 | Glycerol | 0.71 | 8.20 |
|  | 0.95 | Glycerol | 0.27 | 7.93 |
|  | 0.93 | Glycerol | 0.14 | 6.23 |
|  | 0.91 | Glycerol | No Growth | 5.84[2] |
| S. cremoris | 0.998 | Control[3] | 1.00 | 8.23 |
|  | 0.99 | Glycerol | 1.00 | 8.34 |
|  | 0.97 | Glycerol | 0.56 | 7.95 |
|  | 0.95 | Glycerol | 0.33 | 6.45 |
|  | 0.93 | Glycerol | No Growth | 4.41[2] |
|  | 0.91 | Glycerol | No Growth | 4.41[2] |

[1] Maximum number of organisms per volume of nutrient medium
[2] Initial inoculum count
[3] Nutrient medium without humectant

TABLE 3

| Bacteria | $A_w$ Value | Humectant | Growth Rate Div./Hr. | Log Max. No./ml.[1] |
|---|---|---|---|---|
| S. diacetylactis | 0.998 | Control[3] | 1.00 | 8.25 |
|  | 0.99 | Sucrose | 1.00 | 8.63 |
|  | 0.97 | Sucrose | 0.71 | 7.11 |
|  | 0.95 | Sucrose | 0.24 | 4.76 |
|  | 0.93 | Sucrose | No Growth | 4.76[2] |
|  | 0.91 | Sucrose | No Growth | 4.76[2] |
| S. lactis | 0.998 | Control[3] | 1.00 | 8.40 |
|  | 0.99 | Sucrose | 1.00 | 8.70 |
|  | 0.97 | Sucrose | 0.22 | 8.93 |
|  | 0.95 | Sucrose | No Growth | 4.87[2] |
|  | 0.93 | Sucrose | No Growth | 4.87[2] |
|  | 0.91 | Sucrose | No Growth | 4.87[2] |
| S. cremoris | 0.998 | Control[3] | 0.71 | 7.99 |
|  | 0.99 | Sucrose | 0.63 | 7.96 |
|  | 0.97 | Sucrose | 0.01 | 6.69 |
|  | 0.95 | Sucrose | No Growth | 4.38[2] |
|  | 0.93 | Sucrose | No Growth | 4.38[2] |
|  | 0.91 | Sucrose | No Growth | 4.38[2] |

[1] Maximum number of organisms per volume of nutrient medium
[2] Initial inoculum count
[3] Nutrient medium without humectant The growth rate of the bacteria was determined generally according to the method described in Oginsky et al, *Introduction to Bacterial Physiology* (1959), pp 52–56.

As can be seen from Tables 2 and 3, the growth rate for each of the diacetyl-producing bacteria generally decreases as the $a_w$ value of the nutrient medium was lowered whether the humectant was glycerol or sucrose. For glycerol, *S. diacetylactis* and *S. cremoris* evidence no growth at an $a_w$ value of 0.93 with *S. lactis* evidencing no growth at an $a_w$ value of 0.91. In the case of sucrose, *S. lactis* and *S. cremoris* evidenced no growth at an $a_w$ value of 0.95, whereas *S. diacetylactis* evidenced no growth at an $a_w$ value of 0.93.

C. Effect of $A_w$ Values on Diacetyl Production of Diacetyl-Producing Bacteria For each of the nutrient media shown in Tables 2 and 3, the diacetyl content thereof was analyzed in triplicate by the procedure described in a publication to Pack et al, "Owades and Jakovac Method for Diacetyl Determination in Mixed Strain Starters", *Journal of Dairy Science*, Vol. 40 (1964), pp. 981–986. The methods described in this publication were altered slightly by the addition of a condenser system to permit better recovery of dimethylglyoxime. Standard curves were established using varying concentrations of glyoxime. The efficacy of the of the recovery procedure was estimated by spiking fresh samples of milk nutrient media with diacetyl. Recovery was greater than 90% in all cases.

The diacetyl levels in the various nutrient media are expressed in terms of total production and production relative to numbers of organisms as shown in the following tables:

TABLE 4

| Bacteria | $A_w$ Value | Humectant | Acidity Max. % Titratable[1] | pH |
|---|---|---|---|---|
| S. diacetylactis | 0.998 | Control[4] | 0.90 | 4.5 |
|  | 0.99 | Glycerol | 0.87 | 4.5 |
|  | 0.97 | Glycerol | 0.78 | 4.6 |
|  | 0.95 | Glycerol | 0.60 | 4.8 |
|  | 0.93 | Glycerol | None | 6.9 |
|  | 0.91 | Glycerol | None | 6.9 |
| S. lactis | 0.998 | Control[4] | 0.95 | 4.4 |
|  | 0.99 | Glycerol | 0.94 | 4.4 |
|  | 0.97 | Glycerol | 0.87 | 4.5 |
|  | 0.95 | Glycerol | 0.74 | 4.6 |
|  | 0.93 | Glycerol | None | 6.9 |
|  | 0.91 | Glycerol | None | 6.9 |
| S. cremoris | 0.998 | Control[4] | 0.84 | 4.5 |
|  | 0.99 | Glycerol | 0.80 | 4.5 |
|  | 0.97 | Glycerol | 0.72 | 4.6 |
|  | 0.95 | Glycerol | 0.23 | 6.2 |
|  | 0.93 | Glycerol | None | 7.0 |
|  | 0.91 | Glycerol | None | 7.0 |

| Bacteria | $A_w$ Value | $\mu g./20$ ml.[2] | Diacetyl Production $\mu g./10^8$[3] |
|---|---|---|---|
| S. diacetylactis | 0.998 | 31.7 | 0.71 |
|  | 0.99 | 29.5 | 0.65 |
|  | 0.97 | 60.1 | 1.34 |
|  | 0.95 | 100.3 | 2.50 |
|  | 0.93 | 0 | 0 |
|  | 0.91 | 0 | 0 |
| S. lactis | 0.998 | 7.9 | 0.02 |
|  | 0.99 | 4.9 | 0.10 |
|  | 0.97 | 45.5 | 7.08 |
|  | 0.95 | 39.5 | 10.04 |
|  | 0.93 | 0 | 0 |
|  | 0.91 | 0 | 0 |
| S. cremoris | 0.998 | 2.4 | 0.01 |
|  | 0.99 | 3.2 | 0.01 |
|  | 0.97 | 22.3 | 0.13 |
|  | 0.95 | 4.5 | 3.20 |
|  | 0.93 | 0 | 0 |

TABLE 4-continued

| | 0.91 | 0 | 0 |

[1] Calculated as lactic acid
[2] Diacetyl produced per volume of nutrient medium
[3] Diacetyl produced per organism
[4] Nutrient medium without humectant

TABLE 5

| Bacteria | $A_w$ Value | Humectant | Acidity Max. % Titratable[1] | pH |
|---|---|---|---|---|
| S. diacetylactis | 0.998 | Control[4] | 0.88 | 4.6 |
| | 0.99 | Sucrose | 0.79 | 4.6 |
| | 0.97 | Sucrose | 0.58 | 4.9 |
| | 0.95 | Sucrose | 0.12 | 6.6 |
| | 0.93 | Sucrose | None | 7.0 |
| | 0.91 | Sucrose | None | 7.0 |
| S. lactis | 0.998 | Control[4] | 0.90 | 4.4 |
| | 0.99 | Sucrose | 0.90 | 4.3 |
| | 0.97 | Sucrose | 0.83 | 4.3 |
| | 0.95 | Sucrose | None | 7.0 |
| | 0.93 | Sucrose | None | 7.0 |
| | 0.91 | Sucrose | None | 7.0 |
| S. cremoris | 0.998 | Control[4] | 0.80 | 4.6 |
| | 0.99 | Sucrose | 0.73 | 4.6 |
| | 0.97 | Sucrose | 0.49 | 4.9 |
| | 0.95 | Sucrose | None | 7.0 |
| | 0.93 | Sucrose | None | 7.0 |
| | 0.91 | Sucrose | None | 7.0 |

| Bacteria | $A_w$ Value | g./20 ml.[2] | Diacetyl Production g./10[8][3] |
|---|---|---|---|
| S. diacetylacits | 0.998 | 72.5 | 0.20 |
| | 0.99 | 209.9 | 0.24 |
| | 0.97 | 42.7 | 0.17 |
| | 0.95 | — | — |
| | 0.93 | 0 | 0 |
| | 0.91 | 0 | 0 |
| S. lactis | 0.998 | 0 | 0 |
| | 0.99 | 26.4 | 0.03 |
| | 0.97 | 40.6 | 0.24 |
| | 0.95 | 0 | 0 |
| | 0.93 | 0 | 0 |
| | 0.91 | 0 | 0 |
| S.cremoris | 0.998 | 8.1 | 0.05 |
| | 0.99 | 21.6 | 0.11 |
| | 0.97 | 12.4 | 1.38 |
| | 0.95 | 0 | 0 |
| | 0.93 | 0 | 0 |
| | 0.91 | 0 | 0 |

[1] Calculated as lactic acid
[2] Diacetyl produced per volume of nutrient medium
[3] Diacetyl produced per organism
[4] Nutrient medium without humectant The titratable acidity, expressed as lactic acid, was measured by titrating a 0.1053 Normal sodium hydroxide solution to a pH end point of 8.0. The pH of nutrient media aliquots prior to titration was also measured. Titratable acidity is generally reflective of how energetic the bacterial culture is.

Attention is directed to the column in Tables 4 and 5 referring to diacetyl production per volume of nutrient medium.

In the case of glycerol (Table 4), diacetyl production was improved for nutrient media having $a_w$ values of 0.95 and 0.97 with diacetyl production being also increased for S. cremoris in a nutrient medium having an $a_w$ value of 0.99 compared to the control nutrient medium. In the case of sucrose (Table 5), diacetyl production was increased for S. lactis and S. cremoris at $a_w$ values of 0.97 and 0.99 with diacetyl production being increased for S. diacetylactis at an $a_w$ value of 0.99 compared to the control nutrient medium.

What is claimed is:

1. A diacetyl-producing composition, comprising:
    (a) an aqueous nutrient medium having a pH of about 4.5 to 7.0 and containing a metabolizable amount of diacetyl precursor;
    (b) a diacetyl-producing bacteria selected from the group consisting of S. diacetylactis, S. cremoris, S. lactis and mixtures thereof; and
    (c) sucrose in an amount sufficient to lower the $a_w$ value of said nutrient medium to from about 0.95 to 0.99 and to increase the diacetyl production of said bacteria per volume of said nutrient medium.

2. A composition according to claim 1 wherein the amount of said precursor is from about 0.1 to 1.0% by weight of said nutrient medium.

3. A composition according to claim 2 wherein said nutrient medium comprises milk having up to about 2% butterfat.

4. A composition according to claim 3 wherein said precursor is selected from the group consisting of citric acid, bacteriologically acceptable salts of citric acid and mixtures thereof.

5. A composition according to claim 4 wherein said bacteria is S. diacetylactis.

6. A composition according to claim 4 wherein said bacteria is S. cremoris.

7. A composition according to claim 4 wherein said bacteria is S. lactis.

8. A method for increasing the diacetyl production of a diacetyl-producing bacteria selected from the group consisting of S. diacetylactis, S. cremoris, S. lactis and mixtures thereof, the bacteria being inoculated into an aqueous nutrient medium having a pH of from about 4.5 to 7.0 and containing a metabolizable amount of a diacetyl precursor, said method comprising the steps of:
    (a) incorporating in the nutrient medium prior to inoculation of the bacteria a humectant selected from the group consisting of glycerol, sucrose and mixtures thereof in an amount sufficient to lower the $a_w$ value of the nutrient medium to from about 0.95 to 0.99 and to increase the diacetyl production of the bacteria per volume of the nutrient medium; and
    (b) incubating the inoculated nutrient medium after step (a) at a temperature of from about 28° to 37° C. to produce the diacetyl.

9. A method according to claim 8 wherein the nutrient medium comprises milk having up to about 2% butterfat.

10. A method according to claim 9 wherein the precursor is selected from the group consisting of citric acid, bacteriologically acceptable salts of citric acid and mixtures thereof.

11. A method according to claim 10 wherein the humectant is glycerol in an amount sufficient to lower the $a_w$ value of the nutrient medium to from about 0.95 to 0.97.

12. A method according to claim 11 wherein the bacteria is S. diacetylactis.

13. A method according to claim 11 wherein the bacteria is S. cremoris.

14. A method according to claim 11 wherein the bacteria is S. lactis.

15. A method according to claim 10 wherein the humectant is sucrose in an amount sufficient to lower the $a_w$ value of the nutrient medium to from about 0.97 to 0.99.

16. A method according to claim 15 wherein the bacteria is S. diacetylactis.

17. A method according to claim 15 wherein the bacteria is S. cremoris.

18. A method according to claim 15 wherein the bacteria is S. lactis.

* * * * *